US00PP28044P3

(12) United States Plant Patent
Olesen

(10) Patent No.: US PP28,044 P3
(45) Date of Patent: May 23, 2017

(54) MINIATURE ROSE PLANT NAMED 'POULPAR090'

(50) Latin Name: ***Rosa* hybrid**
Varietal Denomination: Poulpar090

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 14/756,251

(22) Filed: Aug. 20, 2015

(65) Prior Publication Data

US 2017/0055387 P1 Feb. 23, 2017

(51) Int. Cl.
*A01H 5/02* (2006.01)

(52) U.S. Cl.
USPC ..... Plt./118

(58) Field of Classification Search
USPC ..... Plt./118
See application file for complete search history.

(56) References Cited

PUBLICATIONS

PLUTO Plant Variety Database Aug. 2, 2016. p. 1.*
Indoor Roses . Main varieties 2013 by Poulsen.*

* cited by examiner

*Primary Examiner* — Annette Para

(57) ABSTRACT

A new garden rose plant of the Miniature class which has abundant, apricot flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar090'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulpar090', originated as a single seedling from the stated cross.

The new variety may be distinguished from its male pollen parent and female seed parent primarily by the following characteristics. The male pollen parent has fewer flower buds on a flowering branch than the new variety. The female seed parent has yellow flowers, while the new variety has apricot flowers.

The objective of the hybridization of this rose variety was to create a new and distinct variety for garden use with unique qualities, such as:

1. Uniform and abundant apricot flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpar090' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulpar090' was selected in the spring of 2008 by the inventor as a single plant from the progeny of the aforementioned hybridization.

Asexual reproduction of 'Poulpar090' by traditional budding and rooted cuttings was first done by Mogens N. Olesen in the nursery in Fredensborg, Denmark in July, 2008. This initial and other subsequent asexual propagations conducted in controlled environments have demonstrated that the characteristics of 'Poulpar090' are true to type and are transmitted from one generation to the next.

Description of the Drawing

The accompanying color illustrations show as true as is reasonably possible to obtain in color photographs of this type, the typical characteristics of the buds, flowers, leaves, and stems, of 'Poulpar090'.

Specifically illustrated in FIG. 1 are flower petals detached, open flower, leaves, bare stem with cluster of flower buds, sepals detached, and reproductive flower parts.

Figure 1:
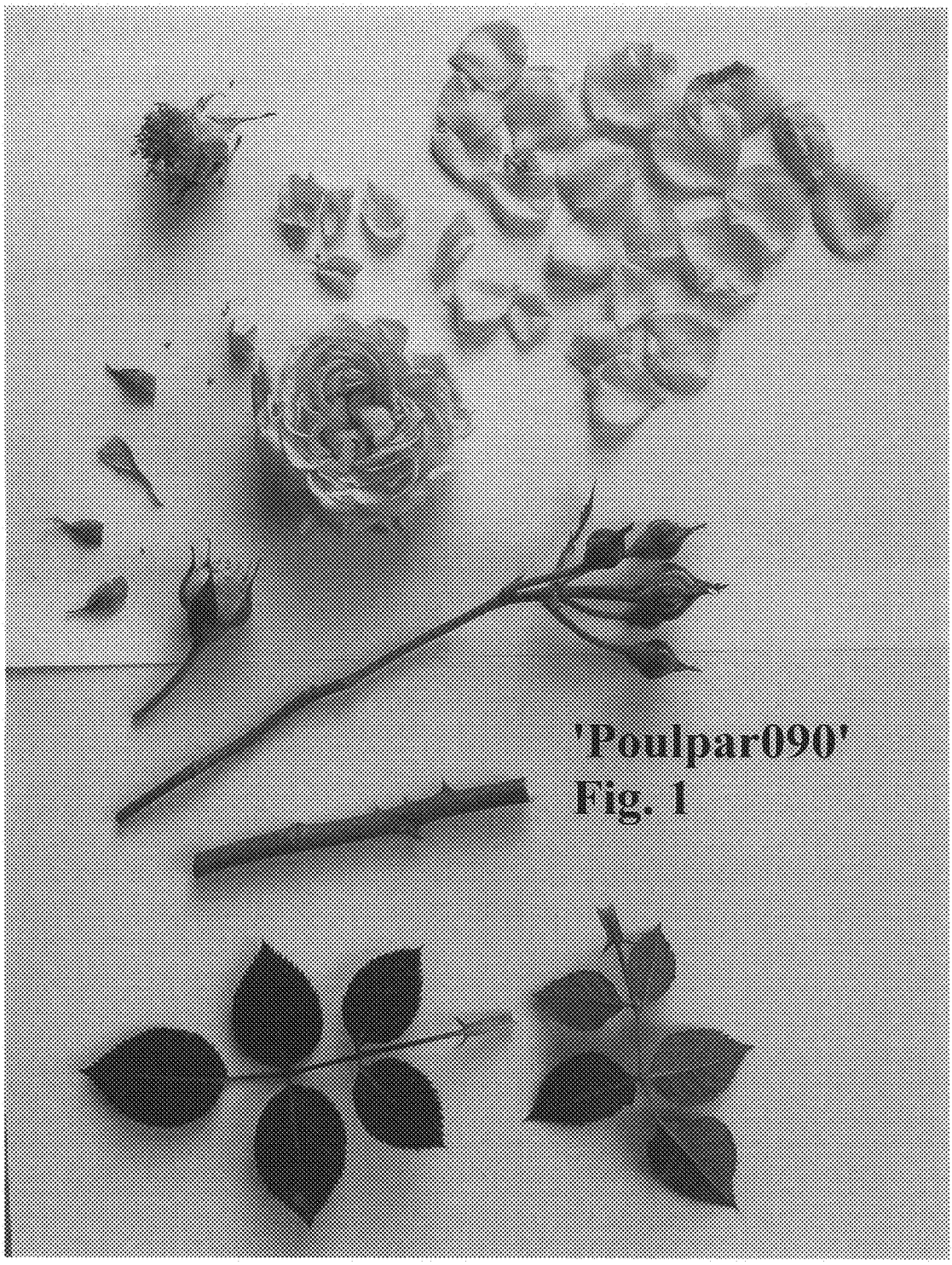
Figure 2:
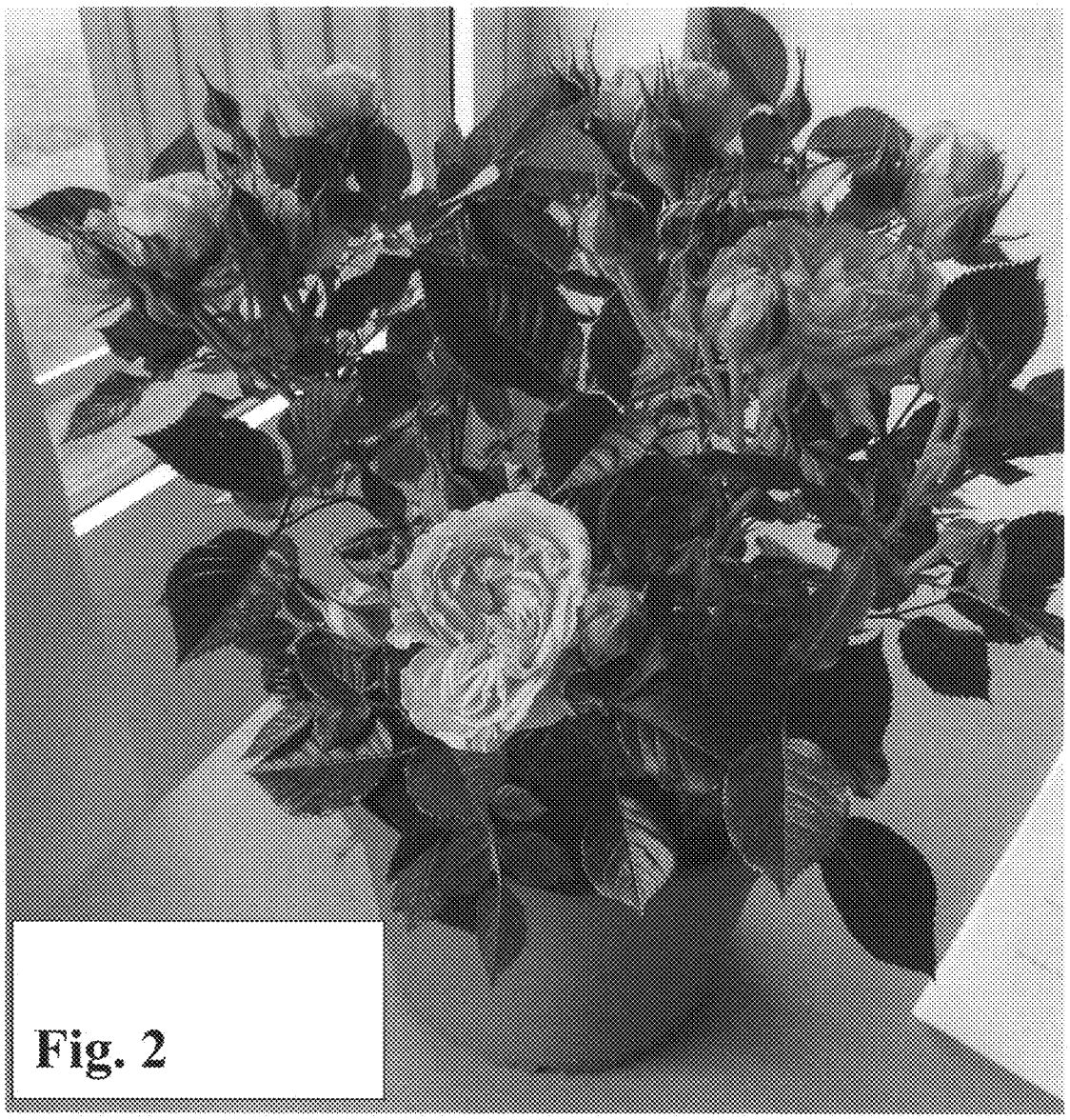

Specifically illustrated in FIG. 2 is a whole flowering plant in a container. Plants shown are 1 year of age.

Detailed Description of the Variety

The following is a description of 'Poulpar090',as observed in its growth in in an open air container nursery in Denmark. Observed plants are 1 year of age, and were grown on their own roots in 21 cm container. Color references are made using The Royal Horticultural Society (London, England) Colour Chart, 2001, except where common terms of color are used.

For a comparison, several physical characteristics of the rose variety 'Poulpar071', U.S. Plant Pat. No. 24,549 are compared to 'Poulpar090' in Chart 1.

CHART 1

| | 'Poulpar090' | 'Poulpar071' |
|---|---|---|
| Petal Count | 80 | 70 |
| Flower Diameter | 70 mm | 50 to 60 mm |
| General Tonality of Flower Color | Yellow-Orange Group 20D | Orange Red Group 32B |

FLOWER AND FLOWER BUD

Blooming habit: Continuous.

Flower bud:

*Size.*—Upon opening, 20 mm in length from base of receptacle to end of bud. Bud diameter is 12 mm.

*Bud form.*—Urceolate.

*Bud color.*—As sepals divide petals are Yellow-Orange Group 20B.

*Sepal inner surface.*—Color: Yellow-Green Group 147C. Surface: Lightly pubescent.

*Sepal outer surface.*—Color: Yellow-Green Group 144A with intonations of Greyed-Purple Group 184B. Texture: Smooth.

*Sepal shape.*—Apex: Cirrhose. Base: Flat at union with receptacle.

*Sepal margin.*—Margins have very weak foliaceous appendages on three of the five sepals.

*Sepal size.*—22 mm long, 8 mm wide.

*Receptacle.*—Texture: Smooth. Size: 6 mm in height, 12 mm wide. Color: Yellow-Green Group 144B. Shape: Broad funnel.

*Pedicel.*—Surface: Smooth. Length: 20 to 30 mm. Diameter: 3 mm on average. Color: Yellow-Green Group 144B. Strength: Strong.

*Peduncle.*—Length: 5 to 14 cm. Diameter: About 4 mm. Color: Yellow-Green Group 144A. Texture: Smooth.

Flower bud development: Flower buds are borne in panicles of 30 to 40 flower buds per stem.

Flower bloom:

*Fragrance.*—None.

*Duration.*—The blooms have a duration on the plant of approximately 18 days. Petals drop not easy.

*Size.*—Flower diameter is 70 mm when open. Flower depth is 20 mm.

*Flower shape.*—Rosette, very double, flower with many slightly overlapping petals of different sizes.

*Shape of flower, side view.*—The upper and lower portion are flat.

Petalage: Under normal conditions, flowers have 80 petals total, 20 of which are petaloids.

General tonality of flower: Open flowers are Yellow-Orange Group 20D.

Petal color:

*Upon opening, inner and outer petals.*—Upper surface: Yellow-Orange Group 18A. Lower surface: Orange Group 24C.

*After opening, inner and outer petals.*—Upper surface: Yellow-Orange Group 18A. Lower surface: Orange Group 24C.

Petals:

*Petal reflex.*—Weak.

*Margin.*—Entire and uniform. Weak undulations.

*Shape.*—Generally broad elliptic. Apex shape: Rounded. Base shape: Acute.

*Size.*—25 mm (l)×30 mm (w).

*Texture.*—Smooth.

*Thickness.*—Average.

Petaloids:

*Size.*—20 mm (l) by 10 mm (w).

*Quantity.*—About 20.

*Shape.*—Asymmetric and irregular. The apex is acute and rounded. The base is acute.

*Color.*—Upper surface is Yellow-Orange Group 18A. The lower surface is Orange Group 24C.

Reproductive flower parts:

*Pollen.*—None observed.

*Anthers.*—Size: 2 mm in length. Color: Yellow-Orange Group 21A. Quantity: 100 on average.

*Filaments.*—Color: Yellow-Orange Group 21A. Length: 4 mm.

*Pistils.*—Length: 3 mm. Quantity: 45 on average.

*Stigmas.*—Color: Yellow Group 10A.

*Styles.*—Color: Orange-Red Group 31A and Yellow Group 2D.

*Location of stigmas.*—Level relative to the length of the filaments and the height of the anthers.

*Hips.*—None Observed.

PLANT

Plant growth: Upright, bushy. Plants are 25 cm in height, and 30 cm wide.

Stems:

*Color.*—Juvenile growth: Yellow-Green Group 144A. Mature growth: Yellow-Green Group 146B.

*Length.*—On average, canes are 20 cm from the base of the plant to the flowering portion.

*Diameter.*—6 mm.

*Internodes.*—On mature canes about 10 to 30 mm between nodes.

*Surface texture.*—Young wood: Smooth. Older wood: Smooth.

Long prickles:

*Incidence.*—0 to 3 prickles per 10 cm of stem.

*Size.*—Average length of prickles on mature stems is 4 mm.

*Shape.*—Upper portion is concave. Lower portion is concave.

*Color.*—Juvenile prickles: Greyed-Purple Group 185B. Mature prickles: Greyed-Purple Group 185B.

Plant foliage:

*Compound leaf.*—About 100 mm (l)×80 (w).

*Quantity.*—About 2 leaves per 10 cm of stem on average.

*Leaf bearing angle to the stem.*—60 degrees.

*Color of juvenile foliage.*—Upper side: Yellow-Green Group 144A. Lower side: Yellow-Green Group 144B.

*Color of mature foliage.*—Upper side: Yellow-Green Group 147A. Lower side: Yellow-Green Group 147B.

Plant leaves and leaflets:

*Stipules*.—Size: About 20 mm long, 9 mm wide. Quantity: 2 per compound leaf Shape: Linear, slightly broad based with outward extending apices. Margins: Finely serrated. Color: Yellow-Green Group 146C.

*Petiole*.—Length: 11 to 25 mm. Diameter: 1 to 2 mm.

*Upper surface*.—Color: Yellow-Green Group 146A with weak intonations of Greyed-Purple Group 184D.

*Lower surface*.—Color: Yellow-Green Group 144A.

*Rachis*.—Length: 15 to 20 mm. Upper surface: Color: Yellow-Green Group 146A with weak intonations of Greyed-Purple Group 184D.

*Lower surface*.—Color: Yellow-Green Group 144A. Observations: Small prickles.

*Leaflet*.—Quantity: Normally 7 leaflets. Margins: Serrulate. Size: On average terminal leaflets are 45 mm long, 30 mm wide. Shape: Generally ovate. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar090', substantially as illustrated and described herein, due to its abundant apricot flowers, disease resistance, and extended period of bloom.

* * * * *

'Poulpar090'